(12) United States Patent
Levinski et al.

(10) Patent No.: US 8,456,641 B1
(45) Date of Patent: Jun. 4, 2013

(54) OPTICAL SYSTEM

(75) Inventors: Vladimir Levinski, Nazareth (IL); Noah Bareket, Saratoga, CA (US); Michael E. Adel, Zichron (IL)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/303,296

(22) Filed: Nov. 23, 2011

(51) Int. Cl.
*G01N 21/55* (2006.01)

(52) U.S. Cl.
USPC .......................................... 356/445

(58) Field of Classification Search
USPC .......................................... 356/445
See application file for complete search history.

(56) References Cited

U.S. PATENT DOCUMENTS

2007/0090308 A1* 4/2007 Harding .................... 250/559.42
2011/0287387 A1* 11/2011 Chen et al. .................... 433/215

* cited by examiner

*Primary Examiner* — Tu Nguyen
(74) *Attorney, Agent, or Firm* — Luedeka Neely Group, P.C.; Rick Barnes

(57) ABSTRACT

An optical system including a light source, optics for directing illumination, thereby producing reflected light, optics for receiving the reflected light, a splitter disposed at a pupil plane for receiving the reflected light and splitting it into a first and second portion, first imaging optics for receiving the first portion and directing it to a first sensor to produce a first image portion, the first sensor delivering the first image portion to a processor, second imaging optics for receiving the second portion and directing it to a second sensor to produce a second image portion, the second sensor delivering the second image portion to the processor, and the processor for combining the first image portion and the second image portion into a single image of the sample.

13 Claims, 2 Drawing Sheets

OPTICAL SYSTEM

FIELD

This invention relates to the field of optics. More particularly, this invention relates to the optical alignment, registration, and overlay metrology of integrated circuits.

Systems for alignment, registration, and overlay metrology use optical microscopes to image special marks on the substrate. The resulting image is processed to provide the required information. Images are constructed either by using cameras such as charge-coupled devices, or by scanning the mark and constructing a signal with a point detector. Some systems use straightforward microscope imaging systems. Other systems use filtering of diffraction orders as a means for enhancing the contrast of the image or signal.

These prior art systems are susceptible to measurement errors that originate from subtle variations of the target mark construction due to substrate to substrate or site to site process variations. Some errors originate from diffraction effects that modulate the phase of the diffracted light and from inherent asymmetries of the imaging system.

What is needed, therefore, is a system that overcomes problems such as these, at least in part.

SUMMARY OF THE CLAIMS

The above and other needs are met by an optical system for imaging a sample, the optical system including a light source for providing illumination, illumination optics for directing the illumination onto the sample, thereby producing reflected light, receiving optics for receiving the reflected light and directing the reflected light toward a pupil plane, an optical splitter disposed at the pupil plane, for receiving the reflected light at the pupil plane and splitting the reflected light into at least a first light portion and a second light portion, first imaging optics for receiving the first light portion and directing the first light portion to a first image sensor to produce a first image portion, the first image sensor further for delivering the first image portion to a processor, second imaging optics for receiving the second light portion and directing the second light portion to a second image sensor to produce a second image portion, the second image sensor further for delivering the second image portion to the processor, and the processor for receiving the first image portion and the second image portion and combining the first image portion and the second image portion into a single image of the sample.

In this manner, the two image portions in each segmented channel part are processed separately to provide a measurement result for each part of the image, and the results are then averaged by combining them into a single image. Dominant common mode phase errors have an equal and opposite impact on the two image portions, and thus are cancelled out when the images are combined.

In some embodiments the optical splitter splits the reflected light in to a first light portion, a second light portion, a third light portion, and fourth light portion, third imaging optics receive the third light portion and direct the third light portion to a third image sensor to produce a third image portion, the third image sensor further delivers the third image portion to the processor, fourth imaging optics receive the fourth light portion and direct the fourth light portion to a fourth image sensor to produce a fourth image portion, the fourth image sensor further delivers the fourth image portion to the processor, and the processor receives the first image portion, the second image portion, the third image portion, and the fourth image portion and combines the first image portion, the second image portion, the third image portion, and the fourth image portion into a single image of the sample.

In some embodiments the first light portion includes part of a zero order reflection and a plus one refractive order of the reflected light. In some embodiments the second light portion includes part of a zero order reflection and a minus one refractive order of the reflected light. In some embodiments the optical system is part of a substrate inspection system. In some embodiments the optical system is part of a substrate metrology system. In some embodiments the optical system is part of a substrate alignment system. In some embodiments the optical splitter is a prism having two facets at the pupil plane. In some embodiments the optical splitter is a prism having four facets at the pupil plane. In some embodiments the illumination optics have a numerical aperture that is smaller than a numerical aperture of the receiving optics.

According to another aspect of the invention there is described a method for imaging a sample by providing illumination, directing the illumination onto the sample, thereby producing reflected light, receiving the reflected light and directing it toward a pupil plane, receiving the reflected light at the pupil plane with an optical splitter disposed at the pupil plane, and splitting the reflected light into at least a first light portion and a second light portion, receiving the first light portion and directing it to a first image sensor to produce a first image portion, delivering the first image portion to a processor, receiving the second light portion and directing it to a second image sensor to produce a second image portion, delivering the second image portion to the processor, and combining the first image portion and the second image portion into a single image of the sample.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Various embodiments of the present invention improve the accuracy of the imaging systems that are used for the alignment, registration, and overlay metrology of substrates, such as semiconductor wafers.

In some embodiments the illumination system numerical aperture and the imaging system numerical aperture are configured so as to allow separation of the first orders of diffraction at the pupil plane. In some embodiments the pupil is segmented into at least two parts, where each part is directed onto its own imaging detector or camera. When the target image has spatial frequencies along two dimensions, the pupil can be segmented into four parts. Segmentation into two parts is sufficient for linear targets, such as line gratings.

The signals or images in each segmented channel part are processed separately to provide a measurement result for each part, and the measurement results are then averaged. Dominant common mode phase errors have an equal and opposite impact on the measurement results for the two (or more) parts, and thus are cancelled out when the measurement results are averaged.

Figure 4:
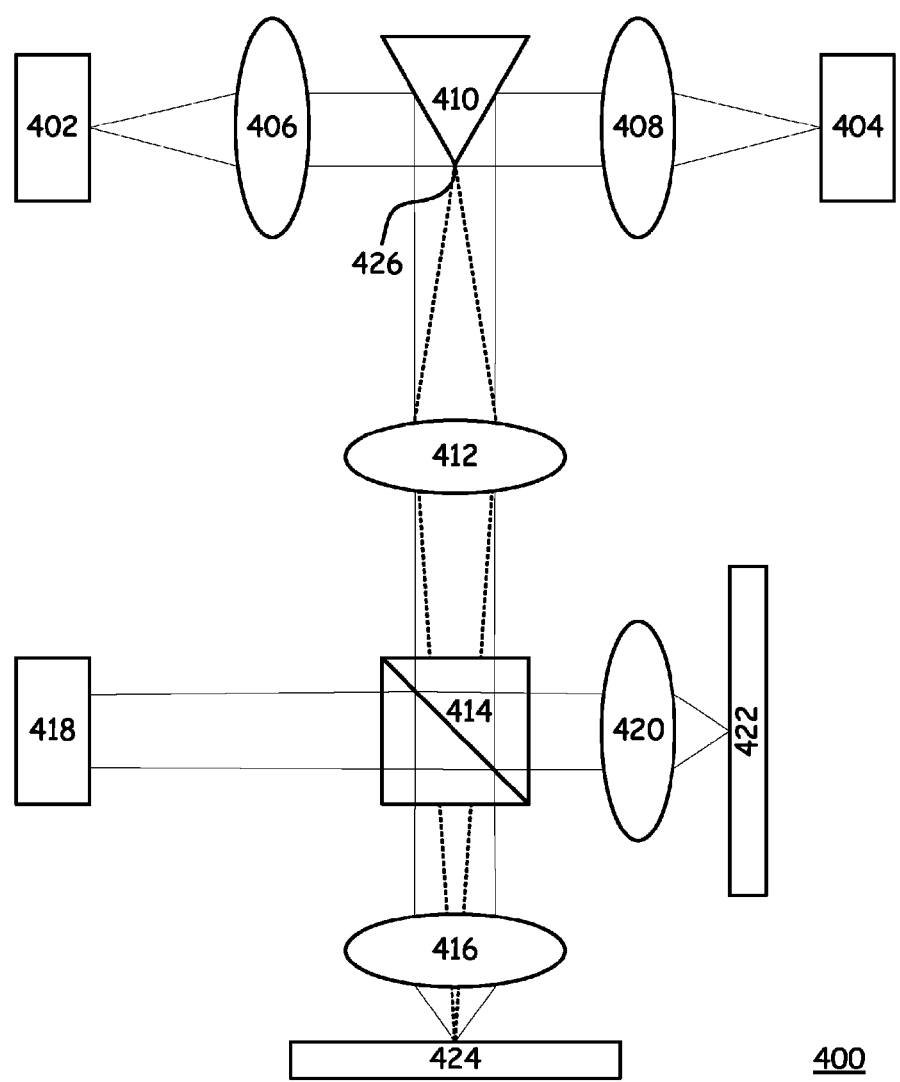
FIG. 4 is a simplified schematic diagram of an apparatus according to an embodiment of the present invention.

FIG. 4 depicts an embodiment of an optical system 400 according to the present invention, which implements pupil splitting. A light source 418 provide light to a beam splitter 414, which directs the light simultaneously through both a reference objective 420 (and onto a reference plane 422) and a main objective 416 (and onto the sample substrate 424). Light reflected from the sample substrate 424 travels back through the main objective 416, the beam splitter 414, a relay lens 412, to a four-way or two way beam splitter 410 (for example).

The optical system 400 has an intermediate pupil plane 426, where the beam splitter 410 is placed, creating (in various embodiments) two or four imaging channels, for example. The beam splitter 410 in one embodiment is a pyramid-prism having four facets, which create four imaging channels. In other embodiments the beam splitter 410 has two facets, which create two imaging channels. Other numbers of facets and imaging channels are also comprehended.

The imaging lenses 406 and 408 focus two of the imaging channels onto cameras 402 and 404. The optics and cameras for the third and fourth imaging channels (if present) that go into the page and out from the page are not depicted. Image processing is applied independently to each of the imaging channels, and the final results are averaged in the X and Y directions.

Figure 1:
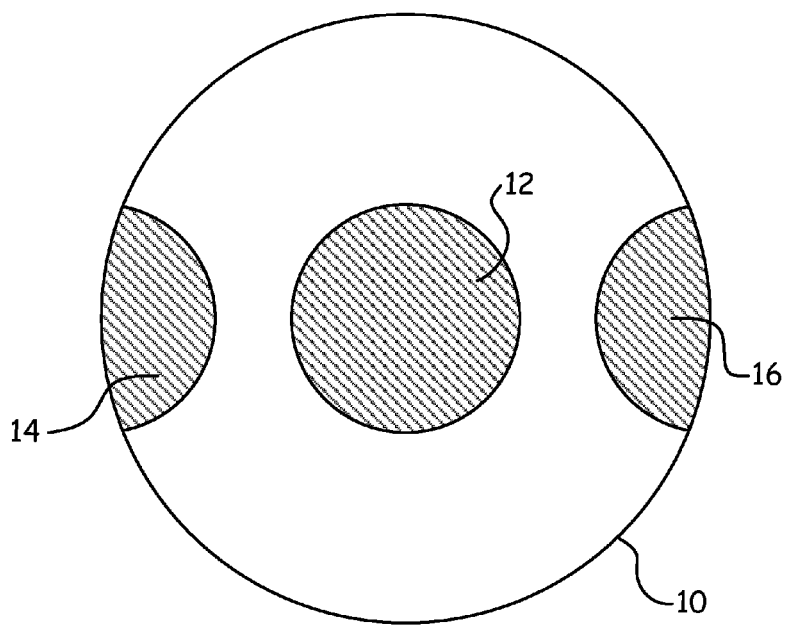
FIG. 1 depicts the zero order reflection and plus/minus first order refractions at the pupil plane according to an embodiment of the present invention.

The operation of the split-pupil imaging system 400 can be illustrated by looking at the distribution of light in the pupil. In a typical sensor of this type, the light reflected back into the pupil includes both the zero order reflection and the diffraction from the grating target 424. One embodiment of a system 400 according to the present invention uses an illumination numerical aperture that is smaller than the collection (imaging) numerical aperture, so the diffraction orders can be substantially separated at the pupil plane. The distribution of light in the pupil 10 will thus appear as depicted in FIG. 1, in which the first orders of diffraction 14 and 16 are separated from the zero order reflection 12.

ANALYSIS OF THE RESULTING IMAGE

A simple embodiment of the invention includes normal illumination, imaging of only zero 12 and first diffraction orders 14 and 16, and a segmented pupil system. Diffraction orders of plus/minus one are almost completely separated in the pupil plane 10, so that pupil segmentation provides separation of the plus one diffraction order 16 and part of the zero order 12 from the minus one diffraction order 14 and the rest of zero order 12. Both separated light fluxes are simultaneously focused on two detectors that output two signals, designated as $I_1(t)$ and $I_2(t)$.

In this embodiment, the image of the grating is created using part of the zero order and minus one diffraction order as a left signal, and the rest of the zero order and the plus one diffraction order as a right signal. As follows from the simplified model given below, the amplitudes of the zero order and diffraction orders are complex and, correspondingly, there is a phase shift between the zero order and first diffraction orders, which is denoted as $\phi$. Due to symmetry, the amplitude of the phase $\phi$ is the same for both the right and the left signals, but the directions of the phase of the signals are opposite one from another (the plus one first diffraction order as the right signal, and the minus one first diffraction order as the left signal). The amplitudes of the left and right signals (up to a non-sufficient complex multiplier) is given as:

$$E_{right} = A_{right} + a_{right} * e^{2\pi i \frac{x}{P} - i \frac{2\pi}{P} * \text{Grid\_Position} + i\Psi + i\Phi}$$

and $$E_{left} = A_{left} + a_{left} * e^{-2\pi i \frac{x}{P} + i \frac{2\pi}{P} * \text{Grid\_Position} - i\Psi + i\Phi},$$

where the phase $\Psi$ accounts for asymmetric lens aberrations. The corresponding intensities as integrated over a spot size that is not equal to a whole number of pitches are given by:

$$I_{right} = I^0_{right} + I^1_{right} * \cos\left[\frac{2\pi}{P} * \text{Grid\_Position} - \Psi - \Phi\right]$$

and $$I_{left} = I^0_{left} + I^1_{left} * \cos\left[\frac{2\pi}{P} * \text{Grid\_Position} - \Psi + \Phi\right]$$

It need not be assumed that $I_{right}^{0,1} = I_{right}^{0,1}$, because each signal can be analyzed separately.

A standard imaging system produces a summarized signal of:

$$I = I_0 + I_1 * \cos\left(\frac{2\pi}{P} * \text{Grid\_Position} - \Psi\right) * \cos(\Phi),$$

and the signal contrast deteriorates because of the topography phase $\phi$. When $\phi$ is close to $\pi/2$, the signal contrast is almost zero. In the present embodiments, there is no signal contrast deterioration.

Analyzing each signal separately yields Phase$_{left}$(t) and Phase$_{right}$(t). A standard N-point phase algorithm designed for phase extraction (with N>3) is used for this purpose.

In other words, signals are measured at different grating positions (as defined by the positions of the spot center) and, knowing the exact values of the steps, the phase at each measured point is calculated. In an embodiment where a scanning microscope is used, signals are measured and averaged over each scanned distance. Accordingly, the measured signal for each interval between the grid positions $x_n$ and $x_{n+1}$ is given as:

$$I_{left,right} = I^0_{left,right} \cdot (x_{n+1} - x_n) +$$
$$I^1_{left,right} \cdot \frac{P}{\pi} \sin\left[\frac{\pi}{P}(x_{n+1} - x_n)\right] \cdot \cos\left[\frac{\pi}{P}(x_{n+1} + x_n) - \Psi \pm \Phi\right],$$

and a grid position in the middle of each interval is found.

The sum of two phases doesn't depend on the topography phase $\phi$, as in the prior art, but a part of the information on the grating position includes some error that is caused by optical aberrations. The last should be independent of process variations, because it depends only on the target pattern in the pupil plane, which is the same for all sites. Therefore, this factor can be removed by using an appropriate calibration procedure.

In this manner, all of the effects of various process variations and optical imperfections can be removed, provided that the illumination direction is substantially perpendicular to the plane of the substrate. Estimates indicate that the illumination numerical aperture should be about 0.1 when a calibration procedure is performed for each process for a very tight spec TIS 3σ of about 0.1 to 0.2 nanometers, and even less than 0.02 to 0.03 when a calibration procedure is performed once per tool for the same spec).

SIMPLIFIED MODEL FOR PHASE TARGET

Figure 2:
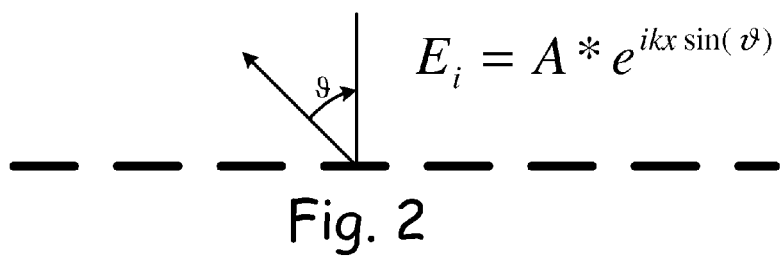
FIG. 2 is a substrate grating surface depicting the incident and reflected light according to an embodiment of the present invention.
Figure 3:
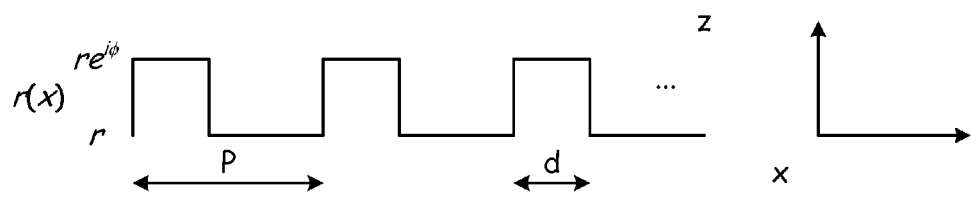
FIG. 3 is the target reflection function for the grating surface of FIG. 2, according to an embodiment of the present invention.

With reference now to FIGS. 2 and 3, an example is given below of an embodiment where a plane wave is scattered on a sample substrate that has a periodically variable thickness, which in the first approximation can be described as a phase object.

The mask has a pitch size P, and the length d of the dark lines is d<P. The light reflecting from the dark lines has a phase shift in comparison to the light reflected from the light lines. The standard phase shift is given as $\phi=\phi(\upsilon,\lambda)$. However, in the present embodiment the target reflection function is as depicted in FIG. 3. After reflection from the sample, the amplitude of the electric field is given as:

$$E_r = A * r(x) * E^{ikx\sin(\vartheta)} = A * r * e^{ikx\sin(\vartheta)} \sum_{n=-\infty}^{n=\infty} f_n e^{i\frac{2\pi}{P}nx},$$

$$f_0 = \frac{de^{i\phi} + P - d}{P}$$

where $f_n = \frac{e^{i\phi}-1}{\pi n}\sin\left(\frac{\pi}{P}nd\right) * e^{-i\frac{2\pi}{P}nGrid\_Position}.$ Accordingly, $$E_r = A * r \sum_{n=-\infty}^{n=\infty} f_n e^{ikx\left[\sin(\vartheta)+\frac{\lambda}{P}n\right]}.$$

$E_r$ is a sum of plane waves corresponding to different diffraction orders. The condition for each one of the waves propagating is given as:

$$-1 < \sin(\vartheta) + \frac{\lambda}{P}n < 1.$$

When the illumination is substantially perpendicular to the surface of the sample Substrate, $\upsilon=0$ and $$2\frac{\lambda}{P} > NA$$

(first order imaging), the amplitude of the reflected electric field is given as:

$$E_r = A_0 + A_1 * e^{i\phi} * e^{i\frac{2\pi}{P}(x-Grid\_Position)} + A_1 * e^{i\phi} * e^{-i\frac{2\pi}{P}(x-Grid\_Position)},$$

where φ is the phase difference between the amplitudes of the zero order and the plus/minus one diffraction orders caused by the sample topography.

Thus, segmented pupil systems according to the present invention alleviate a critical limitation on the accuracy of the overlay metrology systems that are in use today, namely the site-to-site measurement error that is a result of the interaction of target process variation with the inherent asymmetry (aberrations, illumination non-uniformity) of the optical system. In one embodiment the system uses prisms and filters to pick high orders of diffraction that might be less sensitive to process variations. In an embodiment that uses a scanning microscope, the light source is a collimated laser, and single element detectors (such as silicon photodiodes) replace the charge coupled device cameras.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An optical system for imaging a sample, the optical system comprising:
   a light source for providing illumination,
   illumination optics for directing the illumination onto the sample, thereby producing reflected light,
   receiving optics for receiving the reflected light and directing the reflected light toward a pupil plane,
   wherein the illumination optics have a numerical aperture that is smaller than a numeral aperture of the receiving optics, thereby producing at the pupil plane reflected light having first orders of diffraction and a zero order reflection, where all of the first orders of diffraction and a zero order reflection of the reflected light are spatially separated one from another,
   an optical splitter disposed at the pupil plane, for receiving the reflected light at the pupil plane and splitting the reflected light into at least a first light portion and a second light portion,
   first imaging optics for receiving the first light portion and directing the first light portion to a first image sensor to produce a first image portion, the first image sensor further for delivering the first image portion to a processor,
   second imaging optics for receiving the second light portion and directing the second light portion to a second image sensor to produce a second image portion, the second image sensor further for delivering the second image portion to the processor, and
   the processor for receiving the first image portion and the second image portion and combining the first image portion and the second image portion into a single image of the sample.

2. The optical system of claim 1, wherein the first light portion includes part of the zero order reflection and a plus one of the diffraction orders of the reflected light.

3. The optical system of claim 1, wherein the second light portion includes part of the zero order reflection and a minus one of the diffraction orders of the reflected light.

4. The optical system of claim 1, wherein the optical system is part of a substrate inspection system.

5. The optical system of claim 1, wherein the optical system is part of a substrate metrology system.

6. The optical system of claim 1, wherein the optical system is part of a substrate alignment system.

7. The optical system of claim 1, wherein the optical splitter is a prism having two facets at the pupil plane.

8. The optical system of claim 1, wherein the optical splitter is a prism having four facets at the pupil plane.

9. An optical system for imaging a sample, the optical system comprising:
   a light source for providing illumination,
   illumination optics for directing the illumination onto the sample, thereby producing reflected light,
   receiving optics for receiving the reflected light and directing the reflected light toward a pupil plane,
   an optical splitter disposed at the pupil plane, for receiving the reflected light at the pupil plane and splitting the reflected light into at least a first light portion, a second light portion, a third light portion, and fourth light portion,
   first imaging optics for receiving the first light portion and directing the first light portion to a first image sensor to produce a first image portion, the first image sensor further for delivering the first image portion to a processor,
   second imaging optics for receiving the second light portion and directing the second light portion to a second image sensor to produce a second image portion, the second image sensor further for delivering the second image portion to the processor,
   third imaging optics for receiving the third light portion and directing the third light portion to a third image sensor to produce a third image portion, the third image sensor further for delivering the third image portion to the processor,
   fourth imaging optics for receiving the fourth light portion and directing the fourth light portion to a fourth image sensor to produce a fourth image portion, the fourth image sensor further for delivering the fourth image portion to the processor, and
   the processor for receiving the first image portion, the second image portion, the third image portion, and the fourth image portion and combining the first image portion, the second image portion, the third image portion, and the fourth image portion into a single image of the sample.

10. A method for imaging a sample, the method comprising the steps of:
    providing illumination,
    directing the illumination onto the sample with illumination optics, thereby producing reflected light,
    receiving the reflected light with receiving optics and directing the reflected light toward a pupil plane,
    wherein the illumination optics have a numerical aperture that is smaller than a numerical aperture of the receiving optics, thereby producing at the pupil plane reflected light having first orders of diffraction and a zero order reflection, where all of the first orders of diffraction and the zero order reflection of the reflected light are spatially separated one from another,
    receiving the reflected light at the pupil plane with an optical splitter disposed at the pupil plane, and splitting the reflected light into at least a first light portion and a second light portion,
    receiving the first light portion with first imaging optics and directing the first light portion to a first image sensor to produce a first image portion, the first image sensor further for delivering the first image portion to a processor,
    receiving the second light portion with second imaging optics and directing the second light portion to a second image sensor to produce a second image portion, the second image sensor further for delivering the second image portion to the processor, and
    receiving the first image portion and the second image portion with the processor and combining the first image portion and the second image portion into a single image of the sample.

11. The method of claim 10, wherein the first light portion includes part of the zero order reflection and a plus one of the diffracted orders of the reflected light.

12. The method of claim 10, wherein the second light portion includes part of the zero order reflection and a minus one of the diffracted orders of the reflected light.

13. A method for imaging a sample, the method comprising the steps of:
    providing illumination,
    directing the illumination onto the sample with illumination optics, thereby producing reflected light,
    receiving the reflected light with receiving optics and directing the reflected light toward a pupil plane,
    receiving the reflected light at the pupil plane with an optical splitter dispoded at the pupil plane, and splitting the reflected light into at least a first light portion, a second light portion, a third light portion, and fourth light portion,
    receiving the first portion with first imaging optics and directing the first light portion to a first image sensor to produce a first image portion, the first image sensor further for delivering the first image portion to a processor,
    receiving the second light portion with second imaging optics and directing the second light portion to a second image sensor to produce a second image portion, the second image sensor further for delivering the second image portion to the processor,
    receiving the third light portion with third imaging optics and directing the third light portion to a third image sensor to produce a third image portion, the third image sensor further delivering the third image portion to the processor,
    receiving the fourth light portion with fourth imaging optics and directing the fourth light portion to a fourth image sensor to produce a fourth image portion, the fourth image sensor further delivering the fourth image portion to the processor, and
    receiving the first image portion, the second image portion, the third image portion, and the fourth image portion with the processor and combining the first image portion, the second image portion, the third image portion, and the fourth image portion into a single image of the sample.

* * * * *